United States Patent
McKay (10) Patent No.: US 8,900,617 B2
(45) Date of Patent: Dec. 2, 2014

(54) BIO-REMODABLE BONE AUGMENTATION DEVICE AND METHOD

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 101 days.

(21) Appl. No.: 13/188,135

(22) Filed: Jul. 21, 2011

(65) Prior Publication Data

US 2013/0022661 A1 Jan. 24, 2013

(51) Int. Cl.
| | |
|---|---|
| *A61F 2/28* | (2006.01) |
| *A61K 31/573* | (2006.01) |
| *A61K 45/06* | (2006.01) |
| *A61K 31/519* | (2006.01) |
| *A61K 31/436* | (2006.01) |
| *A61K 31/7036* | (2006.01) |

(52) U.S. Cl.
CPC .............. *A61K 45/06* (2013.01); *A61K 31/573* (2013.01); *A61K 31/519* (2013.01); *A61K 31/436* (2013.01); *A61K 31/7036* (2013.01)
USPC ....................................................... 424/423

(58) Field of Classification Search
None
See application file for complete search history.

(56) References Cited

U.S. PATENT DOCUMENTS

| | | | |
|---|---|---|---|
| 5,824,088 A | 10/1998 | Kirsch | |
| 6,049,026 A * | 4/2000 | Muschler | ..................... 424/93.7 |
| 6,328,765 B1 | 12/2001 | Hardwick et al. | |
| 6,409,764 B1 | 6/2002 | White et al. | |
| 6,605,090 B1 | 8/2003 | Trieu et al. | |
| 6,989,029 B2 | 1/2006 | Bonutti | |
| 7,641,690 B2 | 1/2010 | Abdou | |
| 7,855,062 B2 | 12/2010 | Harlow et al. | |
| 2009/0024147 A1 * | 1/2009 | Ralph et al. | ................... 606/151 |
| 2012/0258178 A1 * | 10/2012 | Benham et al. | ............... 424/549 |

OTHER PUBLICATIONS

Woodruff et al., The return of a forgotten polymer-Polycaprolactone in the 21st century, Progress in polymer Science, 2010.*

* cited by examiner

*Primary Examiner* — Anand Desai
*Assistant Examiner* — Melissa Mercier
(74) *Attorney, Agent, or Firm* — Sorell Lenna & Schmidt LLP (57) ABSTRACT

A bio-remodable augmentation device including an implantable member configured for maintaining space in a bone defect. The implantable member is formed from a bio-remodable composite having structural properties so as to aid in the generation of new bone tissue and eventually be reabsorbed in the newly formed bone tissue. This structural and bio-remodable implant reduces, if not eliminates, the need to remove the implantable member from the patient once new bone tissue is formed. A kit including the implantable devices and bone growth material is disclosed. Methods of use are also disclosed.

13 Claims, 6 Drawing Sheets

BIO-REMODABLE BONE AUGMENTATION DEVICE AND METHOD

TECHNICAL FIELD

The present disclosure generally relates to medical devices for the treatment of bone defects, for example, orthopaedic and oral maxillofacial disorders, and more particularly to a bone augmentation device and method including a bio-remodable space maintenance member configured to support bone regeneration.

BACKGROUND

Surgical repair and/or reconstruction procedures including those employing implants are widely used in orthopaedic and oral maxillofacial procedures for bone restoration and repair. These procedures are often used to treat bone defects and disorders, which may result and/or be caused from bone trauma, tumors, infections, tooth loss and other complications. New bone growth is often desired to repair a defect or to build up the existing or remaining bone.

In some cases, a ridge augmentation procedure is employed to add bone height to the jaw in order to be able to place dental implants. Similar procedures can be used in connection with cranial or long bones defects in order to correct a defect or to strengthen or build up the existing bone. Such procedures can employ a spacing device to facilitate bone growth. After new bone has formed, the devices employed during the augmentation are removed. However, the removal of these devices can cause tissue disruption that undesirably exposes new bone and disrupts vascularity leading to associated complications, or can be difficult to remove due to bone overgrowth. This disclosure describes an improvement over these prior art technologies.

SUMMARY OF THE INVENTION

Accordingly, a bio-remodable bone augmentation device and method is provided for treating bone defects by maintaining space in a bone defect to assure proper bone regeneration and in a desired volume. It is contemplated that the bone augmentation device is made from a composition having structural properties and is bio-remodable so that the implant slowly becomes incorporated into the newly regenerated bone and does not have to be removed. The bio-remodable implant is configured to promote bone growth and since it does not have to removed, it keeps tissue disruption to a minimum.

In one particular embodiment, in accordance with the principles of the present disclosure, a bio-remodable bone augmentation device is provided. The bio-remodable bone augmentation device comprises an implantable member configured for maintaining space in a bone defect. The implantable member is formed from a bio-remodable composite having structural properties and is configured to maintain space in a bone defect so as to aid in the regeneration of new bone tissue. The implantable member is also configured so that it can become incorporated in the newly regenerated bone thereby eliminating the need to remove the implantable member once new bone is formed.

In one particular embodiment, in accordance with the principles of the present disclosure, the bio-remodable composite from which the bio-remodable bone augmentation device is made comprises at least one material selected from the group consisting of collagen, nondemineralized bone, substantially fully demineralized bone, partially demineralized bone, superficially demineralized bone, human allograft collagen and bone composite materials with structural properties, ceramic and collagen material with structural properties, ceramics, natural polymers, biocompatible materials, biodegradable materials, bio-remodable materials, biologically absorbable materials, bioerodable materials, bone, autograft, metal, and polymers. These materials are not only biocompatible but are also or bio-remodable and provide support while new bone tissue is regenerated.

In one particular embodiment, in accordance with the principles of the present invention, the bone augmentation device is made from a bio-remodable bone/collagen composite material that can be formed into any shape with the strength needed for the uses in this patent application and is available from Osteotech, Inc. The composite used contains bone particles in a collagen solution that immediately precipitates into composite putty. The water in the composition is then forced out under compression and forms a hard structural implant that is used according to the description provided herein. Alternative compositions can be used that include synthetic ceramic in place of or in addition to bone particles in the bio-remodable composition described herein. Similarly, the bio-remodable composition can use bone animal derived collagen or recombinantly produced collagen.

In one embodiment of the present invention, the implantable member of the augmentation device of the present invention is shaped in the form of a perforated concave shield having a plurality of pores or perforations therethrough. The shape provides space for the new tissue to regenerate and reduces overlying muscle forces and allows for blood vessels and tissue to extend within the space provided for new tissue growth. These properties enhance new bone formation.

In yet another embodiment of the present invention, the implantable member of the augmentation device of the present invention is shaped in the form of a perforated hollow cylindrical shaped member having a plurality of holes therethrough. As with the shield, the cylindrical shaped member is configured to protect bone growth material from compression and migration in, long bone, spinal, oralmaxillofacial, and cranial bone defects and fractures so as to enhance new bone formation.

In yet another embodiment of the present invention, the implantable member of the augmentation device of the present invention is an oral maxillofacial device configured for increasing the height of a jaw ridge due to missing teeth. The oral maxillofacial device is U-shaped so as to fit over the jaw ridge defect and is made from the bone/collagen composite material described herein. In one embodiment of the present invention the u-shaped implant is packed with additional bone graft material so as to build up the jaw ridge to facilitate tooth implants.

The present invention also provides a kit for generating bone in a mammal in order to correct a bone defect or to strengthen weakened bone tissue. The kit comprises at least two implantable members configured for maintaining space in a bone defect according to the present invention. Various sizes and shapes of the implantable members of the present invention can be provided. In addition a single sheet of the implantable member can be provided that can be cut and configured to meet the needs of a particular situation by the surgeon while performing the procedure. The kit may also provide at least one bone growth promoting material in sufficient quantity to be used with the implantable member in order to form clinically efficacious bone graft.

In one embodiment of the present invention, a method for implanting at least one implantable member according to the present invention into a bone defect is provided. The method comprises implanting at least one implantable member in a bone defect, depositing bone growth material about said implanted member and allowing the bone growth material to form bone tissue. As the bone tissue is regenerated, the biologically absorbable implantable member(s) are absorbed or remodeled into the newly regenerated bone tissue providing not only support and mass but eliminating the need for removing the implant. This eliminates the amount of tissue disruption that can occur with the removal of the device.

BRIEF DESCRIPTION OF THE DRAWINGS

The present disclosure will become more readily apparent from the specific description accompanied by the following drawings, in which.

DETAILED DESCRIPTION OF THE INVENTION

The exemplary embodiments of the bone augmentation device and methods of use disclosed are discussed in terms of medical devices for the treatment of bone disorders, for example, orthopaedic and oral maxillofacial bone defects such as cranial plate and long bone defects. The bone augmentation device of the present disclosure is biodegradable or bio-remodable so that it eventually reabsorbs into the newly formed bone tissue and does not have to be removed. It is envisioned that the bone augmentation device maintains space when attempting to grow new bone either in a defect and/or building up a jawbone in a ridge augmentation procedure in preparation for implants. It is further envisioned that the bone augmentation device is employed with bone growth material that is retained within the defect while preventing overlying soft tissue and muscle forces from compressing newly forming bone tissue. It is contemplated that the bone augmentation device of the present invention may be configured as a sheath with and without perforations, a cylindrical tubular structure with and without perforations, as well as a curved or flat moldable structure, which can interlock with each other to provide additional mechanical support. The implant may also be provided as a moldable sheet that can be cut to size by the surgeon either before or during the procedure. The implantable device is made from a collagen and bone composition that is absorbable, moldable and provides structural integrity to the implant.

It is envisioned that the implant described in the present disclosure may be employed to treat oral maxillofacial bone defects. It is also contemplated that the implant described in the present disclosure may be employed to fix cranial plate defects, bone fractures, spinal fusion procedures, reduced density, replace diseased bone tissue and correct long bone defects. The implantable devices and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "superior" and "inferior" are relative and used only in the context to the other, and are not necessarily "upper" and "lower".

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

The headings in this application are not meant to limit the disclosure in any way; embodiments under any one heading may be used in conjunction with embodiments under any other heading.

It is noted that, as used in this specification and the appended claims, the singular forms "a," "an," and "the," include plural referents unless expressly and unequivocally limited to one referent. Thus, for example, reference to "an intervertebral disc implant" includes one, two, three or more intervertebral disc implants.

The term "practitioner" or "user" means a person who is using the methods and/or devices of the current disclosure on the patient. This term includes, without limitation, doctors (e.g., surgeons, interventional specialists, physicians), nurses, nurse practitioners, other medical personnel, clinicians, dentists, veterinarians, or scientists.

The term "therapeutic agent" may be used interchangeably herein with the terms "drug," "therapeutically effective amount," and "active pharmaceutical ingredient" or "antibiotics." It will be understood that unless otherwise specified a "therapeutic agent" formulation may include more than one therapeutic agent, wherein exemplary combinations of therapeutic agents include a combination of two or more drugs. The therapeutic agent provides a concentration gradient of the therapeutic agent for delivery to the site.

A "therapeutically effective amount" or "effective amount" is such that when administered, the drug results in alteration of the biological activity, such as, for example, inhibition of inflammation, reduction or alleviation of swelling or inflammation in or near the bone defect or diseased bone etc.

The term "biodegradable" includes that all or part of the implant will degrade over time by the action of enzymes, by hydrolytic action and/or by other similar mechanisms in the bone defect area. In various embodiments, "biodegradable" includes that the implant or part of the implant (e.g., microparticle, microsphere, etc. incorporated into the inner or outer layer of the implant) can break down or degrade within the area of implant (i.e. in or near the bone defect area etc.) to non-toxic components after or while newly formed bone is generated. By "bioerodible" it is meant that the implant or portion thereof will erode or degrade over time due, at least in part, to contact with substances found in the surrounding tissue, fluids or by cellular action. By "bioresorbable" it is meant that the implant or portion thereof will be broken down and resorbed within the human body, for example, by a cell or tissue. "Biocompatible" means that the implant will not cause substantial tissue irritation or necrosis at the target tissue site.

The term "bio-remodable" includes that all or part of the implant will degrade over time by the action of enzymes, by hydrolytic action and/or by other similar mechanisms in the bone defect area and is naturally remodeled by osteoclasts and osteoblasts into the newly formed bone. This composite material can be formed into a given shape prior to implant that provides structural integrity and does not have to be removed once implanted since it naturally forms into new bone. That is, the material will provide structural support as the new bone forms underneath it and it is slowly replaced by creeping substitution only during the bone remodeling phase, ultimately resulting in the desired volume of new bone and no implant to later remove.

The terms "regeneration", "formation", "production", reformation", and "restoration" used herein in means the production, restoration or generation of living bone or periodontal tissue. Living bone tissue here refers to the level of biological organization representing the major components of bone including bone cells that are generally located within a matrix of mineralized collagen; blood vessels that provide nutrition for the bone cells; and may include fatty bone marrow and/or cells that give rise to components of blood.

The phrases "sustained release" and "sustain release" (also referred to as extended release or controlled release) are used herein to refer to one or more therapeutic agent(s) that is introduced into the bone defect area of a human or other mammal and continuously or continually releases a stream of one or more therapeutic agents over a predetermined time period and at a therapeutic level sufficient to achieve a desired therapeutic effect throughout the predetermined time period.

The phrase "immediate release" is used herein to refer to one or more therapeutic agent(s) that is introduced into the bone defect area of a human or other mammal that is allowed to dissolve in or become absorbed at the location to which it is administered, with no intention of delaying or prolonging the dissolution or absorption of the therapeutic agent.

The phrase "delayed release" is used herein to refer to one or more therapeutic agent(s) that is introduced into the bone defect area of a human or other mammal that is allowed to dissolve in or become absorbed at the location to which it is administered, only after an outer layer is compromised with the specific intention of delaying or prolonging the dissolution or absorption of the therapeutic agent, i.e. anti-inflammatory agent.

The following discussion includes a description of a bone augmentation device and related methods of employing the bone augmentation device in accordance with the principles of the present disclosure. Alternate embodiments are also disclosed. Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Figure 1:
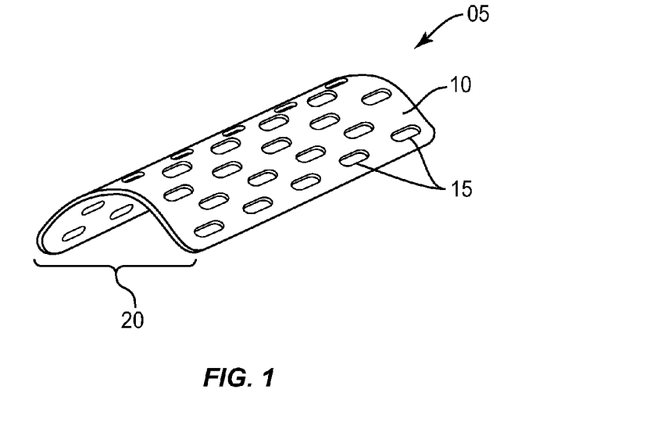
FIG. 1 is a perspective view of one particular embodiment of a bone augmentation device in accordance with the principles of the present disclosure.

Turning now to FIG. 1, which illustrates components of a bone augmentation device 05 in accordance with the principles of the present disclosure. The bone augmentation device 05 is shown in the shape of a sheath or shield having perforations 15 distributed throughout. The sheath or shield 05 can be flat or have a curvature 20 as shown in FIG. 1. The shield is designed to retain bone growth materials in the general area of the bone defect and provide an environment that is conducive for bone tissue regeneration. The perforations or pores 15 distributed throughout the shield 10 are configured to pass through the thickness of the device. The perforations allow blood vessels and cells originating from the living tissues peripheral to the spaces to grow through the perforations and into the bone defect so as to facilitate bone tissue growth. The perforations 15 can be distributed throughout the entire device or can be located in strategic areas and not in others. The diameter of the perforations 15 of the device fall within the range of about 3 micrometers to about 1 centimeter. The size of the diameter used depends on the overall size of the implantable device 05, the intended use of the implantable device 05, the number of perforations and positioning of the perforations on the implantable device 05. An implantable bone augmentation device having no perforations at all also falls within the scope of the present invention.

Figure 2:
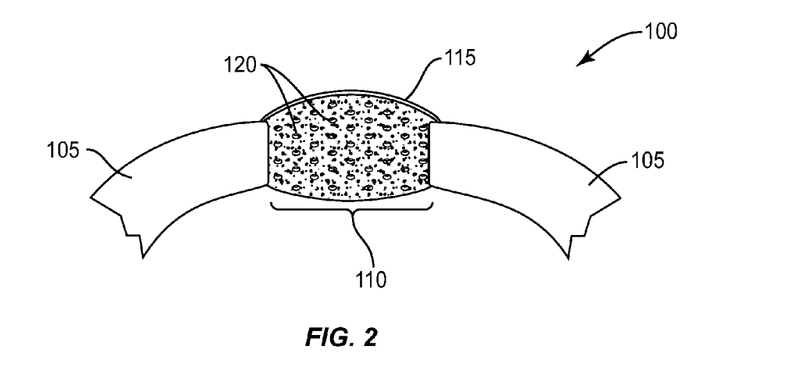
FIG. 2 is a side cutaway view in cross section of a cranial defect and one particular embodiment of a bone augmentation device in accordance with the principles of the present disclosure.

FIG. 2 shows the implantable device 115 of the present invention being used to correct a cranial defect 110. Here, the implantable device 115 is positioned to bridge a defect in a cranial plate 105. Once positioned over the defect bone growth/graft material 120 is deposited within the defect to cause bone reformation. The implant 115 is perforated to allow tissue and blood vessels into the defect so as to facilitate bone tissue growth. The implantable device 115 acts as a shield that retains the graft material in the bone defect area and prevents pressures from outlying muscle tissue on the newly formed bone tissue. As will be further discussed in the section on the materials used to make the implantable device, the implantable device is made from a bio-remodable material that will reabsorb into the newly formed bone tissue and does not have to be removed. In the alternative, a non-perforated implantable device can be used to correct the cranial defect and it is envisioned that this falls within the scope of the present invention.

Figure 3:
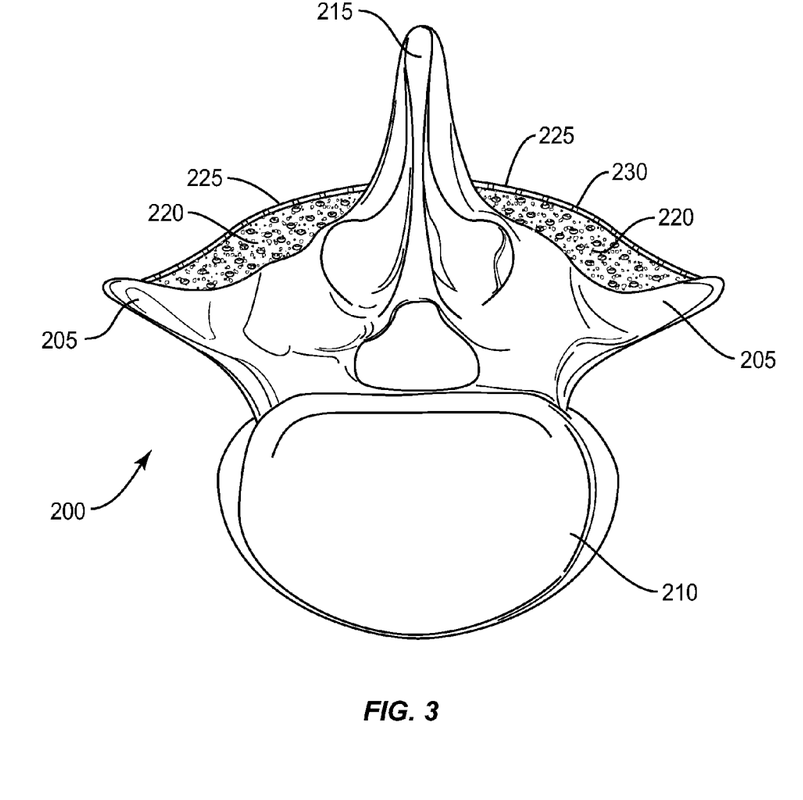
FIG. 3 is a side cutaway view in part cross section of a vertebrae with two bone augmentation devices as shown in FIG. 1.

FIG. 3 shows a cross section of a vertebra 200 orientated so that the posterior portion of the vertebra is at the top of the figure and the anterior portion and body 210 of the vertebrae is at the bottom of the figure. Between the spinous process 215 and the left and right transverse processes 205 is a curved implantable implant 225 positioned so as to form a cavity or pocket so as to retain bone growth material 220 therein. As with the embodiments of the implantable device discussed above, the implantable device 225 can have pores 230 (as shown) or in the alternative not have pores. The implantable device 225 is configured to retain the bone growth material 220 close to the transverse process 205 so as to facilitate bone reformation in order to build up the thickness of the bone graft fusion mass attached to the transverse process. A thicker and larger volume fusion mass provided greater stiffness at that spinal level and therefore better pain relief. The implantable device 225 will eventually be reabsorbed into the newly regenerated bone tissue so as to further thicken the fusion mass along the vertebra. The implantable device 225 can be used on multiple vertebrae at one time in order to increase the thickness and stiffness of the fusion mass at these spinal levels.

Figure 4:
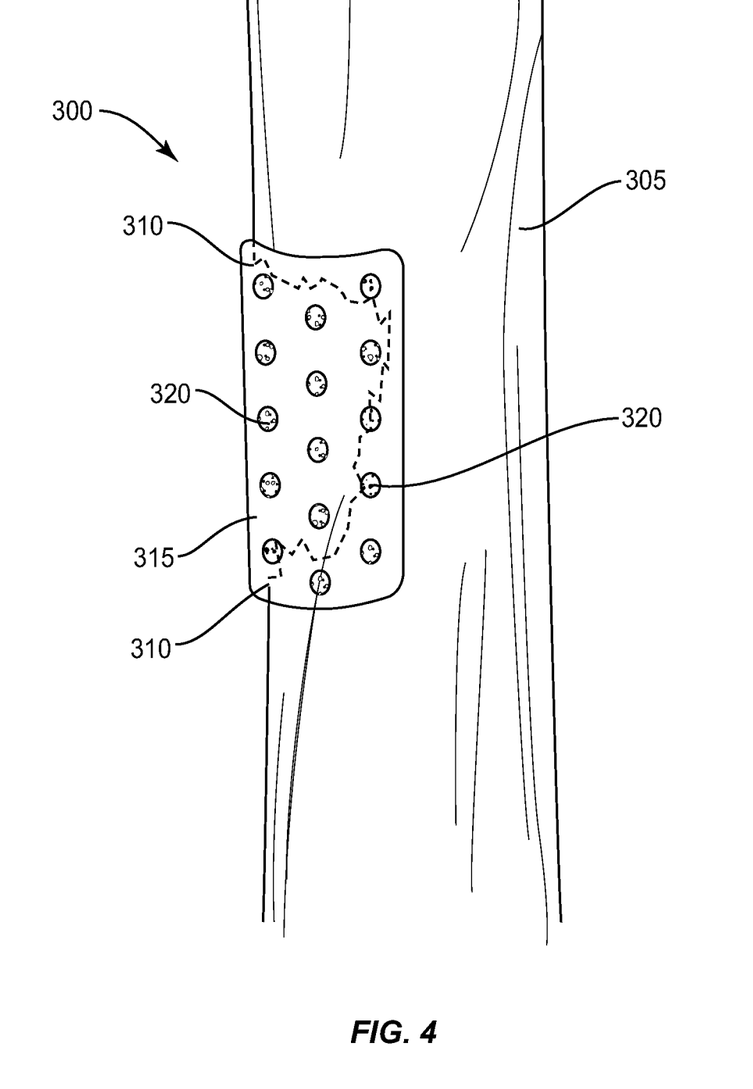
FIG. 4 is a plan view of a long bone having a defect and the bone augmentation device as shown in FIG. 1 positioned to cover the bone defect.

FIG. 4 illustrates a long bone with a defect 300. The defect 310 is shown in a long bone 305 having an implantable device 315 positioned over the defect 310. As with the previous figures the implantable device 315 is shown equipped with pores 320 but can also be used without perforations. The implantable device 315 as shown is curved above the bone defect 310 so as to form a cavity in which bone growth materials 320 can be infused. The implantable device 315 retains the bone growth material 320 so as to facilitate new bone tissue regeneration and provide protect from muscle pressure on the newly formed bone. The implant also provides structural support for the bone while the new bone tissue is being formed, resulting in a larger volume and stronger bone, and eventually becomes reabsorbed in the new bone tissue to add additional support.

Figure 5:
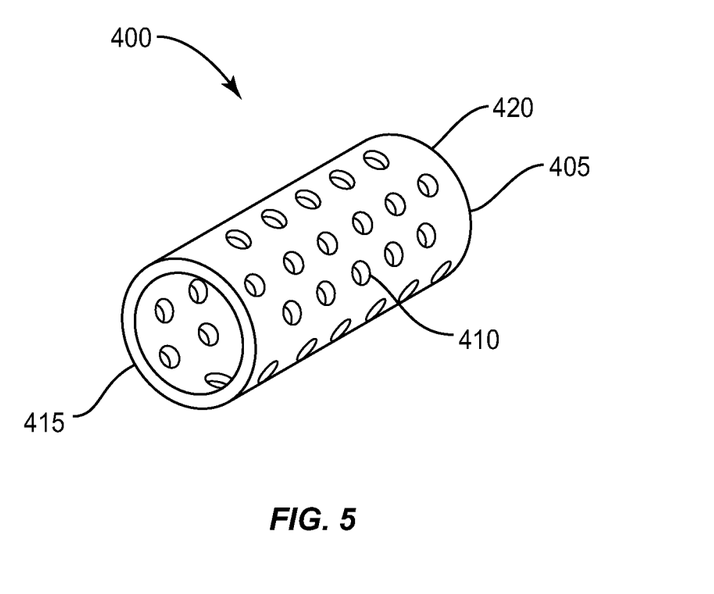
FIG. 5 is a perspective view of a perforated cylindrical shield of the present invention.
Figure 6:
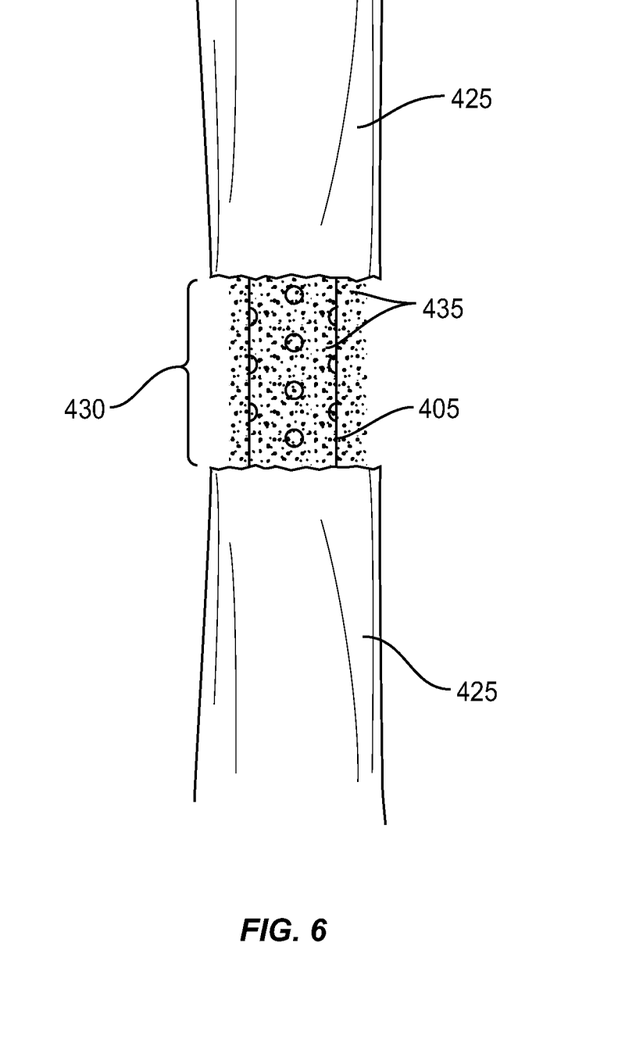
FIG. 6 is a plan view of a long bone complete break having a perforated cylindrical shield positioned with the break with bone growth factors/graft material.

FIG. 5 shows an implantable bone augmentation device of the present invention in the form of a cylindrical tube 400 having a leading edge 415 and a rear edge 405. As with the previous figures, the implantable device 400 can be equipped with perforations 410 but can also be used without perforations. The cylindrical implant 400 is specifically configured to be used in bone defects wherein there is a full separation between the to end portions of a bone, such as in a complete break of a long bone as shown in FIG. 6. In FIG. 6 the bone defect 430 is formed by a complete break of long bone 425 in two segments. This can be either a transverse fracture or a compound fracture wherein the two ends of the bone are cleaned up and the cylindrical implantable device 405 positioned within the bone defect 430. Once in position, bone growth material 435 can be inserted or infused within the cavity created by the device so as to facilitate bone tissue regeneration. Additional bone growth material 435 may be used to facilitate bone tissue regeneration outside of the cylindrical device. The device results in increased new bone volume and strength of the healed long bone.

The diameter of the cylindrical device will vary depending on the long bone in which it will be used or the type of fracture in which it is to be used with. The cylindrical device is preformed into the cylindrical configuration having a defined diameter and since it is made from the bio-remodable composite described herein the cylindrical device provides structural integrity and does not have to be removed once implanted since it naturally forms into newly formed bone. The length of the cylindrical device can also be cut to size during or before the surgical procedure. The thickness of the walls of the cylindrical implantable device will vary according to the structural integrity needed for a particular situation. It is envisioned that the configuration of the implantable device as well as the perforations therein may have alternate configurations, such as, for example, oval, oblong, triangular, square, polygonal, irregular, uniform, non-uniform, offset, staggered, undulating, arcuate, variable and/or tapered.

Figure 7:
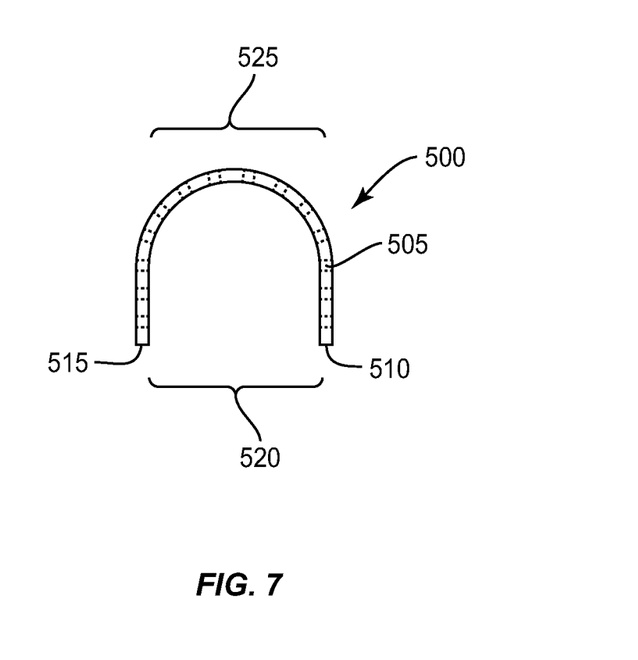
FIG. 7 is a perspective view of an oralmaxillofacial device configured for increasing the height of a jaw ridge.

FIG. 7 shows a perspective view of an implantable oral maximillofacial u-shaped bone augmentation device of the present invention 500 having a first leading edge 510, a second leading edge 515 connected together by a curved edge 525 so as to form a u-shaped implant. Between the first and second leading edges (510 and 515) and below curved edge 525 is a void 520 that is configured to fit over a jaw ridgeline of a patient were a tooth is missing. As with the previous figures, the implantable device 500 can be equipped with perforations 505 but can also be used without perforations. The u-shaped implant 500 is specifically configured to fit over the jaw ridgeline where a tooth is missing so as to repair a defect or to add bone height to the jaw ridgeline of a patient in preparation for a tooth implant. Although a u-shaped oral implant is shown, other shapes and configurations can be used to add bone height to the jaw ridgeline of a patient. As with the other implants described herein, the implant is made from the bio-remodable composite having the properties described herein including the desired structural and bio-remodable properties. The oral implant can also be coated with and/or contain active biological agents which are released into the surrounding area as new bone is formed to provided bone height for a future dental implant.

Also provided is a kit including a plurality of biodegradable or bio-remodable implants of various shapes, thicknesses, and cylindrical diameters are provided along with different types and concentrations of bone growth materials. This kit can be in a pre-sterilized package or can be sterilized prior to use. This kit is designed to provide different implantable devices to a surgeon so that he can best match the device with the particular bone defect.

As stated above, it is essential to the invention that the implantable device having both structural properties as well as be biodegradable or bio-remodable. That is, the implantable device must be strong enough to provide structure for new bone regeneration and to protect new bone tissue from the pressures caused by overlaying muscle. It is also essential that the implantable device be made from a material that will be reabsorbed into the newly formed bone tissue so as to eliminate the need for removal of the implant once new bone tissue is formed. This reduces disruption of not only the newly formed bone tissue but the surrounding soft tissue and vasculature tissue as well.

It is contemplated that the bone augmentation implantable device of the present invention may be fabricated from materials suitable for medical applications, including allograft material such as, nondemineralized bone, substantially fully demineralized bone, partially demineralized bone, superficially demineralized bone or combinations thereof with some structural properties developed and marketed by Osteotech, Inc, as described in U.S. Pat. Nos. 6,440,444; and 6,696,073 and U.S. patent applications Ser. Nos. 11/047,992 and 11/934,980; each of which are incorporated herein in their entirety by reference; ceramics, natural polymers, collagen, biocompatible materials, biodegradable materials, biologically absorbable materials, bioerodable materials, bone, autograft, metal, polymers and/or their composites, depending on the particular application and/or preference of a medical practitioner. For example, the components of the bone augmentation device discussed herein, individually or collectively, can be fabricated from biocompatible materials such as natural polymers including collagen, ceramics, metals and plastic such as stainless steel, titanium, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, rigid polymers including polyphenylene, polyamide, polyimide, polyetherimide, polyethylene epoxy, and composites thereof. Bioabsorbable materials used can be selected from the following polymers: PLA, PLLA, PDLA, PGA, PET, PTFE, PCU, PU, and combinations thereof. Various components of the bone augmentation devices described herein may have material composites, including the above materials, to achieve various desired characteristics such as strength, rigidity, elasticity, compliance, biomechanical performance, durability and radiolucency or imaging preference and biodegradability. The components of bone augmentation device described herein may also include radiolucent materials such as polymers. Radiomarkers may be included for identification under x-ray, fluoroscopy, CT or other imaging techniques.

The biodegradeable material of in, which the implantable bone augmentation device of the present invention is fabricated from, must absorb and incorporate into the newly formed bone and surrounding tissue over time in vivo. Examples, in addition to the ones already discussed include, but are not limited to, polyglycolide, polyactide, polycaprolactone, poly(ethylene glycol), polyurethanes, polyfumarates, polyacrylamides, collagen, silk, polyamines, polysaccharides, tissue or tissue products, and copolymers and blends thereof. It is further contemplated that implantable devices can be adjusted and/or trimmed to the configuration and dimension requirements of a particular application.

It is contemplated that bone growth material used in the present invention may also include therapeutic polynucleotides or polypeptides, which can be packed or otherwise disposed in the bone defect or cylindrical implantable device. It is further contemplated that bone growth material may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within a patient. Suitable biologically active agents include, for example, bone morphogenic protein (BMP), Growth and Differentiation Factors proteins (GDF) and cytokines.

In one embodiment, biologically active agents may be coated onto the exterior of one or all of the components of bone augmentation devices of the present invention for gradual release such as by blending in a bioresorbable polymer that releases the biologically active agent or agents in an appropriate time dependent fashion as the polymer degrades within a patient. Suitable biologically active agents include, for example, bone morphogenic protein (BMP) and cytokines. In the alternative, the bio-remodable material from which the bone augmentation device of the present invention is made may have biologically active agent or agents incorporated directly in the composite material as well. In this configuration, the biologically active agent or agents is/are released as composite material is naturally remodeled by osteoclasts into the newly formed bone One or all of the components of bone augmentation device of the present invention, including bone growth materials may include one or a plurality of agents that can be configured as drug depots with medication for pain and may include antibiotics and/or therapeutics. It is envisioned that the agents may contain active agents and may include one or a plurality of therapeutic agents and/or pharmacological agents for release, including sustained release, to treat, for example, pain, inflammation and degeneration. The agents may include pharmacological agents, such as, for example, antibiotics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressive agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone augmentation device comprising:
   an implantable member configured for maintaining space in a bone defect formed from a bio-remodable composite having structural properties that supports new bone tissue generation and reabsorb into said new bone tissue thereby eliminating the need to remove said implantable member once new bone tissue is formed, wherein the implantable member comprises a first leading edge, a second leading edge connected to the first leading edge by a curved edge so as to form a u-shape, and a void disposed between the first and second leading edges and below the curved edge that is configured to fit over a jaw ridgeline of a patient where a tooth is missing, the implantable member comprising pores extending between the first leading edge and the second leading edge, wherein the bio-remodable composite comprises bone particles in a collagen solution that forms a hard structural implant and is bio-remodable into new bone, and the implantable member comprises polycaprolactone, wherein the implantable member is configured to shield a bone graft material implanted into tissue.

2. The bone augmentation device of claim 1, wherein the implantable member comprises a plurality of holes therethrough so as to enhance new bone tissue formation.

3. The bone augmentation device of claim 1, wherein the bio-remodable composite comprises at least one material selected from the group consisting of nondemineralized bone, substantially fully demineralized bone, partially demineralized bone, superficially demineralized bone, human allograft collagen and bone composite materials with structural properties, ceramics, natural polymers, biocompatible materials, biodegradable materials, biologically absorbable materials, bioerodable materials, autograft, metal, and polymers.

4. The bone augmentation device of claim 1, wherein the at least some of the bone particles of the bio-remodable composite are replaced with synthetic ceramic and at least some of the collagen is replaced with recombinantly produced collagen, animal bone derived collagen, or combinations thereof.

5. The bone augmentation device of claim 1 further comprising bone growth promoting material in sufficient quantity to form clinically efficacious bone graft.

6. The bone augmentation device of claim 5 wherein said bone growth promoting material is selected from a group consisting of biocompatible materials, biocompatible metals and/or rigid polymers, titanium elements, metal powders of titanium or titanium compositions, sterile bone materials, allograft, xenograft materials, synthetic bone materials, coral and calcium compositions, hydroxyapatite, calcium phosphate, calcium sulfite, biologically active agents, bone morphogenic protein (BMP), Growth and Differentiation Factors proteins (GDF), cytokines, nondemineralized bone, substantially fully demineralized bone, partially demineralized bone, superficially demineralized bone or combinations thereof.

7. The bone augmentation device of claim 6 further comprising one or more materials selected from the group consisting of active agents, therapeutic agents, analgesics or anesthetics, immunosuppressives, antibiotics, and pharmacological agents.

8. The bone augmentation device of claim 7 wherein said one or more active agents is selected from the group consisting of antibiotics, anti-inflammatory drugs, steroids, antiviral and anti-retroviral compounds, therapeutic proteins or peptides, therapeutic nucleic acids, and combinations thereof.

9. The bone augmentation device of claim 1 wherein said bone augmentation device is coated with or has incorporated directly in said bio-remodable composite one or more biologically active agents in a degradable polymer so as to provide a gradual release of said biologically active agent or agents in an appropriate time dependent fashion as the polymer degrades within a patient.

10. The bone augmentation device of claim 9 wherein said suitable biologically active agents are selected from the group consisting of bone morphogenic protein (BMP), cytokines, GDF, PDGF, statins, DBM, bone marrow and peptides and combinations thereof.

11. A method of augmenting bone tissue at a surgical site, comprising:
   implanting at least one implantable member of claim 1 at least partially at the bone defect;
   depositing bone graft material about said implantable member;
   allowing the bone graft material to form new bone tissue; and
   checking said implantable member for proper positioning and bone growth after a predetermined period of time, and the implantable member comprises polycaprolactone and the bone defect is located in a jawbone.

12. The bone augmentation device of claim 1, wherein the pores are evenly spaced along the implantation device.

13. The bone augmentation device of claim 1, wherein the pores are between about 3 μm and 1 cm.

* * * * *